United States Patent [19]

Rosenfeld

[11] Patent Number: 4,990,458

[45] Date of Patent: Feb. 5, 1991

[54] DERIVATIZATION OF ORGANIC COMPOUNDS DURING THEIR ANALYSIS OR DETERMINATION

[75] Inventor: Jack M. Rosenfeld, Hamilton, Canada

[73] Assignee: McMaster University, Hamilton, Canada

[21] Appl. No.: 141,983

[22] Filed: Sep. 22, 1987

Related U.S. Application Data

[63] Continuation-in-part of Ser. No. 633,959, Jul. 24, 1984, abandoned, which is a continuation-in-part of Ser. No. 367,941, Apr. 13, 1982, abandoned.

[51] Int. Cl.$^5$ .................... C07C 67/00; C07C 67/10; G01N 30/02; G01N 33/00
[52] U.S. Cl. .................... 436/174; 436/128; 436/129; 436/161; 560/130; 560/204; 560/236; 560/265
[58] Field of Search ............... 436/128, 129, 161, 174; 560/130, 204, 236, 265

[56] References Cited

U.S. PATENT DOCUMENTS

| | | | |
|---|---|---|---|
| 2,283,764 | 5/1942 | Rosenbach et al. | 560/236 |
| 3,148,200 | 9/1964 | Mills et al. | 560/236 |
| 3,278,569 | 10/1966 | Simon et al. | 560/236 |
| 3,461,156 | 8/1969 | Fierce | 560/236 |
| 3,562,315 | 2/1971 | Cookson et al. | 560/236 |
| 3,634,474 | 1/1972 | Hay et al. | 560/236 |
| 4,140,652 | 2/1979 | Korshak et al. | 252/426 |
| 4,332,738 | 1/1982 | Benitez et al. | 560/265 |

FOREIGN PATENT DOCUMENTS

| | | | |
|---|---|---|---|
| 0010479 | 6/1966 | Japan | 560/265 |
| 0015238 | 4/1974 | Japan | 436/20 |

OTHER PUBLICATIONS

Rosenfeld et al., "Solid-Supported Reagents in the Determination of Cannabinoids in Plasma", Anatytical Chemistry, 1986, 54, 716, (published 4/4/86).
Rosenfeld et al., Analytical Chemistry, 58, 716 and 3044, 1986.
Sussman, "Ind. & Eng. Chem.", vol. 38, 1946, pp. 1228-1230.
J. Rosenfeld, "The Cannabinoids: Chemical, Pharmacologic, and Therapeutic Aspects", 1984, pp. 151-161.
Rosenfeld et al., "Analytical Chemistry", Apr. 1976, vol. 48, pp. 726-729.
Rosenfeld et al., "Journal of Chromatography", 283, (1984), pp. 127-135.
Kennedy, "I & EC Research and Development", Mar. 1973, vol. 12, pp. 56-61.
Gustafson et al., "Interactions Responsible for the Selective Adsorption of Organics on Organic Surfaces", 1971, pp. 213-237.
"Technical Bulletin Fluid Process Chemicals, AMBERLITE® XAD-7", Rohm & Haas, undated, pp. 1-11.
"Organic Removal", Rohm & Haas, February 1979.
"Technical Bulletin Fluid Process Chemicals, AMBERLITE® XAD-2", Rohm & Haas, Nov. 1978, pp. 1-12.
Levesque et al., Industrial & Engineering Chemistry, vol. 40, No. 1, pp. 96-99, (1948).
Saletan, Dissertation Abstracts, vol. 12, pp. 275-276, (1952).
Knapp, "Handbook of Analytical Derivatization Reactions," John Wiley & Sons, N.Y., 1979, pp. 146-151 & 183-185.

*Primary Examiner*—Robert J. Warden
*Assistant Examiner*—Kimberly A. Trautman

[57] ABSTRACT

A process for forming derivatives of organic compounds as a step during their analysis. A macroreticular resin is used as both an adsorbent for the analyte and the derivatizing reagent and also as a catalyst for the derivatization reaction. Subsequent serial elution of the absorbed compounds leads to simple separation of the derivatized analyte from the starting materials. Further, the resin impregnated with derivatizing reagent can be used to combine the extraction and derivatization of the analyte. As macroreticular resins are relatively inexpensive, they result in reduced costs compared with conventional catalysts, and their ease of separation from liquid systems makes them easy to use and makes it possible to automate the procedure.

22 Claims, 8 Drawing Sheets

DERIVATIZATION OF ORGANIC COMPOUNDS DURING THEIR ANALYSIS OR DETERMINATION

CROSS-REFERENCE TO RELATED APPLICATION

The present application is a continuation-in-part of my U.S. patent application Ser. No. 633,959 filed on July 24, 1984, now abandoned, which was itself a continuation-in-part of my U.S. patent application Ser. No. 367,941 filed on Apr. 13, 1982, now abandoned.

BACKGROUND OF THE INVENTION

I. Field of the Invention

This invention relates to the formation of derivatives of organic compounds and, more particularly, to such derivatization carried out as a step during highly sensitive analysis or determination of various organic compounds available in very dilute aqueous solutions.

II. Description of the Prior Art

In recent years, techniques have been developed for the analysis or determination of organic compounds present in extremely small quantities or at very low concentrations. For example, by combining gas chromatography with electron capture detection or mass spectrometry operating in the negative ion chemical ionization mode, organic chemicals present in solution at concentrations of micrograms per ml or less can be analysed. Such techniques are extremely useful for the analysis of so-called "biological matrices", i.e. aqueous fluids obtained from living organisms, such as plasma, serum, urine etc. from man and animals and fluid media from microorganisms. A great deal of information can be learned about the organisms if the organic chemicals present in such fluids, often in only trace quantities, can be analysed or determined.

A characteristic of such highly sensitive techniques is that they require the presence of certain specific groups in the molecule, e.g. chromophores, fluorophores or electrophores. For example, electron capture detection requires the presence of an electrophore (a group capable of capturing electrons), e.g. a group containing halogen atoms covalently bound to carbon. Unfortunately many organic compounds of interest for analysis, particularly those from biological matrices, do not possess such groups and must be converted to suitable derivatives as a preliminary step. In some cases it is also necessary to convert unstable compounds to stable derivatives.

As an example, organic chemicals containing carboxylic acid groups may be converted to trichloroethyl or pentafluorobenzyl esters, and compounds containing amino or hydroxyl groups may be converted to trifluoroacyl or pentafluorobenzyl derivatives. This introduces electrophores suitable for highly sensitive analysis and makes the compounds more suitable for purification or separation by gas chromatography.

Derivatization of organic compounds occurring in biological matrices has followed two general approaches in the past. In the first approach, the organic compound to be analysed or determined (the analyte) is first isolated from the biological matrix, concentrated, derivatized by reaction with a derivatizing agent in the presence of a catalyst and then purified. In the second approach, the analyte is simultaneously extracted and derivatized by the use of a plurality of liquid phases and a phase transfer catalyst, followed by purification.

These two conventional approaches have significant disadvantages, the main ones being that they are labour intensive and do not easily lend themselves to automation. Both approaches involve liquid/liquid phase separations and evaporation steps that are not easy to carry out automatically. Moreover, phase transfer catalysts tend to be isolated along with the resulting derivative and the presence of such catalysts interferes with the subsequent analysis. Further, the catalysts themselves tend to be expensive and difficult to use.

Various partial solutions have been found to resolve these problems. Solid/liquid extraction methods have been developed to permit automated isolation of an underivatized analyte. However, these methods still require a separate derivitization step to be carried out on the analyte prior to analysis. In the case of phase transfer catalysts, methods have been developed to remove traces of the catalysts isolated with the derivative, but these methods require extra steps in a procedure designed to simplify sample preparation. Phase transfer catalysts have also been covalently linked to insoluble supports, such as polystyrene or silica gel, and the resulting mechanism of triphasic catalysts has been extensively studied, but these techniques have not as yet been applied to analytical chemistry.

Reference is made to "Mass Fragmentographic Assay for 11-hydroxy-$\Delta^9$-tetrahydro-cannabinol from Plasma" by J. M. Rosenfeld and V. Y. Taguchi, Analytical Chemistry, Vol. 48, pp. 726 to 792, April 1976, as an example showing a conventional derivatization technique.

An object of the invention is therefore to overcome at least some of the disadvantages of the prior art by providing a simplified derivatization technique that can, if desired, be carried out automatically.

SUMMARY OF THE INVENTION

According to one aspect of the invention there is provided in a process for converting an organic compound having a reactive group into a derivative thereof which is suitable for analysis or determination by highly sensitive techniques, wherein said organic compound is contacted with a derivatizing agent capable of reacting with said group in the presence of a catalyst, the improvement which comprises carrying out said derivatizing reaction in aqueous solution in the presence, as said catalyst, of a water-insoluble, non-ionic macroreticular resin capable of adsorbing the analyte from the aqueous solution.

The macroreticular resin is preferably first contacted with a solution of the derivatization reagent in order to impregnate the resin with the reagent. If desired, the impregnated resin can then be separated from the solution and dried prior to use in the extraction/derivatization process.

According to another aspect of the invention there is provided a derivatizing material for organic compounds, comprising a macroreticular resin capable of adsorbing the organic compounds from aqueous solution, having a derivatizing reagent for the organic compound adsorbed thereon.

According to yet another aspect of the invention there is provided an analytical kit comprising a prepackaged quantity of the derivatizing material.

DETAILED DESCRIPTION OF THE INVENTION AND THE PREFERRED EMBODIMENTS

Figures 1, 1A:
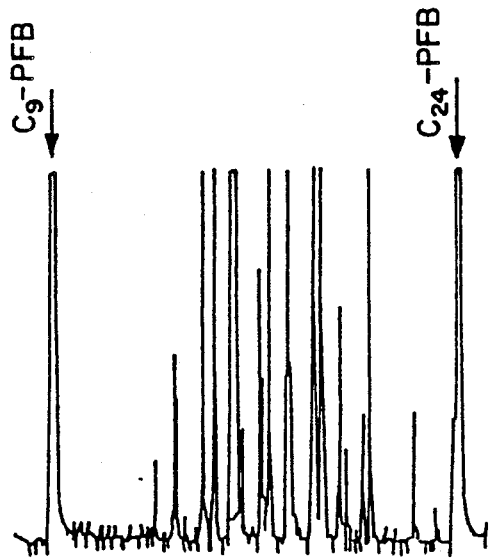
FIG. 1 is a series of gas chromatographic profiles of the hydrosylates of the bacterium *Staph. aureus,* profiles A-1 and A-2 having been obtained by conventional derivatization and profiles B-1 and B-2 having been obtained by derivatization by methods according to the invention.
Figures 1, 1A, 2:
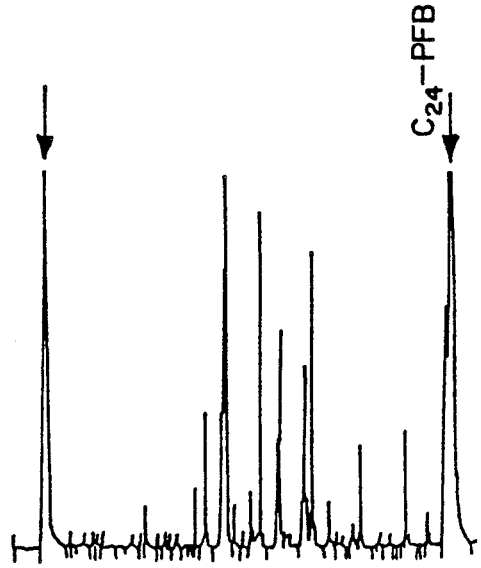
Figures 1, 1B:
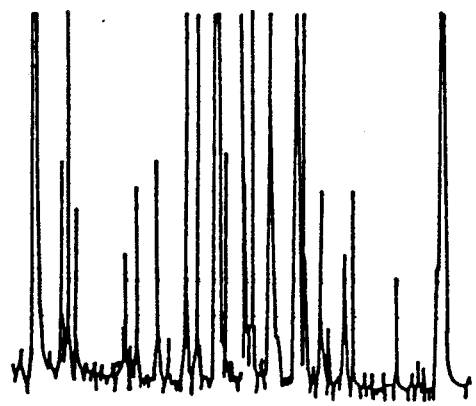
Figures 1, 1B, 2:
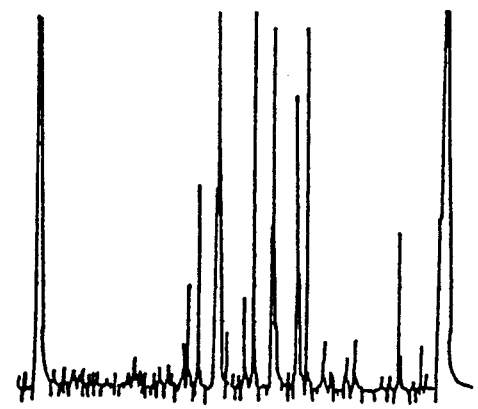

The present invention is based on the unexpected finding that macroreticular resins which are capable of adsorbing an analyte from an aqueous solution, are also capable of catalysing the reaction between such an analyte and a derivatizing agent therefor. Thus, there is no need for a conventional catalyst and, further, the resin acts both as an adsorbent for extraction of the analyte from aqueous solutions and in some instances as a solid chromatographic medium for separation of the derivatized analyte from the starting materials and reaction mixture. As these separations involve liquid/solid partition, automatic techniques can readily be employed. For example, the macroreticular resin impregnated with derivatizing agent can be located in a chromatography column to which the analyte solution is automatically fed, followed by automatic delivery of washing solution and eluants.

To be effective as a catalyst, the resin should be capable of adsorbing the analyte from aqueous solution and preferably should be capable of readily desorbing the analyte or its derivative by elution with common solvents. Clearly, those resins which are unsuited for adsorption from aqueous solution should be avoided. For example, certain known macroreticular resins used for adsorption of materials from gases may not be effective in the present invention.

Suitable non-ionic macroreticular resins are already in common use as adsorbents but, in contrast to certain ion exchange resins, their surfaces were previously thought to be chemically inert. These materials are non-ionic, hard, insoluble, synthetic polymers preferably prepared as beads and are characterized by a wide range of surface polarities, large surface area and various porosities and poresize distributions. The effectiveness of these resins in the present invention is made even more surprising by the fact that ionic resins previously known to have catalytic effects for other types of reaction have been found generally to have no catalytic effects for the types of reaction to which the present invention is applicable, particularly reactions carried out in aqueous solutions. It is believed that non-ionic resins act as adsorbents because van der Waal's interactions take place between the reagents and resin, and because of their very large surface areas resulting from the reticular structure. Most commonly, the resins are polystyrenes, preferably polystyrene-divinylbenzene copolymers, or polymethacrylate materials preferably cross-linked with a suitable non-aromatic comonomer or copolymer such as linoleic acid or polybutadiene etc., although other materials suitable as macroreticular adsorbents may be employed. Typically, but not necessarily, the resins have a porosity in the range of about 0.35 to 0.55 ml/ml, a surface area in the range of about 100 to 1000 $m^2/g$ and an average pore diameter in the range of about 50 to 200 A. The beads typically, but not necesarily, have a diameter in the range of 20 to 60 mesh (0.85 to 0.2 mm) and, because of the cross-linking in the resin, they are substantially insoluble in most aqueous solvents (including acids and bases) and most organic solvents, making them extremely useful for adsorption and chromatographic separation because a variety of solvents and eluants can be employed.

The resin may simply be contacted with a solution of the analyte and derivatizing agent, but it is preferred to impregnate the resin with the derivatizing agent and then contact the impregnated resin with the solution of the analyte.

The concentration of the analyte in the aqueous solution is not particularly important and may range from the nanogram per ml level up to the maximum concentration of the analyte in the solution. For naturally occurring analytes, concentrations are generally 50 μg per ml or less (usually significantly less). The lower concentration limit is really that at which the derivatized analyte ceases to be detectable by the analytical techniques employed.

The amount of macroreticular resin employed is not particularly important and the optimum amount can easily be found by simple experimentation. Usually the resin is present in substantial excess in order to make it easy to remove from solution by filtration etc. Preferably the ratio of resin to derivatizing agent should not be so low that the resin is completely saturated by the derivatizing agent as this may leave little surface area for adsorption of the analyte.

Since the resin acts as an adsorbent for the analyte, it is possible, at least in some forms of the invention, to contact the impregnated resin directly with a biological matrix containing the analyte to bring about both extraction and a derivatization reaction in a single step, thus avoiding separate extraction and concentration steps. It is found that the catalytic action of the resin is often substantially unaffected by the impurities and other compounds present in the biological matrix and that the yield of derivatized analyte is generally independent of the concentration of analyte in the sample.

Even when the catalytic action is adversely affected by the presence of materials in the biological matrix, it has been found that simple pre-treatment of the matrix can often overcome the problem. For example, if proteins present in the matrix interfere with the process, the proteins can first be precipitated by known techniques.

If desired, however, the analyte can first be separated from the biological matrix and adsorbed onto the resin from, for example, a buffered aqueous solution. The known properties of the analytes can also be used to effect purification. Thus, in the case of carboxylic acids present in plasma, it is known that the acids can be adsorbed onto macroreticular resin from an acidic medium and can be desorbed into alkaline phase. The plasma can therefore be acidified and unimpregnated resin added. The resin can then be isolated by filtration, washed and the analyte eluted with a buffer solution having an alkaline pH. The eluate is then free of proteins, basic and neutral constituents. The purified eluant can then be used with the impregnated resin to bring about derivatization. This approach is somewhat longer than direct derivatization but it is still compatible with automation because all steps involve solid/liquid phase separations.

The fact that the macroreticular resins act as a catalyst as well as a support for the analyte and derivatization reagent is apparent because these starting materials, which generally do not react together to a significant extent in mild conditions in the absence of a catalyst, are caused to react together in the presence of the resin.

This enables the extraction/derivatization step to be carried out at low temperatures and in very dilute aqueous solution usually without the need for co-solvents or the like. Thus the method is particularly suited to the derivatization of naturally occurring analytes present at very high dilutions (e.g. micrograms or less per ml, as noted above) in aqueous solutions obtained from biological sources. The derivatization step proceeds quickly (generally under one hour) in high yield (generally 70 to 100% theoretical) under mild conditions.

The reason for this catalytic action of the resin is not known precisely, but it is believed to be due to physical rather than chemical action, because the precise chemical nature of the resin does not apppear to be important to the catalytic activity provided the resin has good adsorbent properties for both the analyte and derivatizing reagent.

A mechanism based on a surface reaction model analagous to alumina catalysed alkylations is postulated (cf article by G. H. Posner, Angew. Chem. Int. Ed. Engl. 17, 487–496, 1978). In this model, the reaction requires adsorption at a reactive site on the resin. This site is a region of the surface that is only partially coated with the reagent. Thus, it is believed adsorption of the analyte occurs in an uncoated area of the surface, but in sufficient proximity to the adsorbed reagent that reaction can occur.

A second property which may be important is the formation of a double layer. For instance, ionized organic molecules are absorbed on the surface of the resin via their hydrophobic moiety. The ionized end protrudes into the solution and forms a layer of water that is attracted to the charged region. This formation of double layer is typical of most macroreticular resins. It is further implied in the article by Posner referred to above that the surface of the alumina provides a region whose dielectric constant is such that it favours formation of the product.

Although the macroreticular resins appear to catalyse the derivatization reaction, they are otherwise unreactive so that labile reagents and derivatives are not generally subjected to degradative reactions.

Preferred examples of the macroreticular resins that can be employed in this invention are the AMBERLITE ®XAD series of resins manufactured and sold by the Rohm & Haas Company of Philadelphia, P.A. Of these resins, AMBERLITE ®XAD 2 is the most preferred, this being a styrene-divinylbenzene type copolymer having a porosity of about 0.42 ml/ml, a surface area of about 300 m$^2$/g, an average particle diameter of about 0.4 mm and an average pore diameter of about 90 Å.

Other satisfactory resins of this type are AMBERLITE ®XAD 4, AMBERLITE ®XAD 7 and AMBERLITE ®XAD 8. XAD 4 is also a styrene-divinylbenzene type copolymer having a porosity of about 0.55 ml/ml, a surface area of about 860 m$^2$/g and an average pore diameter of about 51 Å. XAD-7 and XAD 8 are methacrylate based polymer resins. XAD 7 has an average particle diameter of 0.30 to 0.45 mm, a surface area of about 450 m$^2$/g and an average pore diameter of about 80Å. XAD 8 has a particle diameter of 20 to 60 mesh, a surface area of about 140 m$^2$/g and an average pore diameter of 250Å.

All of these resins are non-ionic, chemically inert (i.e. they do not change chemically in the conditions encountered in the invention) and water-insoluble. They are also capable of acting as adsorbents for the various analytes from aqueous solutions.

The macroreticular resins have the advantages that, in most cases, they are relatively inexpensive compared with conventional derivatization catalysts and they are also reusable. The resins are already in extensive use in semi-automated and automated extraction methods, which methods can readily be adapted to the extraction/derivatization technique of this invention.

The invention can be used for the derivatization of many organic compounds with various known derivatizing reagents e.g. benzyl bromide, pentafluorobenzyl bromide, methyl iodide and alpha, para-dibromoacetophenone. However, of particular importance is the derivatization of carboxylic acids, phenols and amines. Carboxylic acids are generally esterified, whereas the phenols and amines are converted to the ether and N-substituted derivatives. When highly sensitive analysis is required, the carboxylic acids are converted to pentafluorobenzyl esters and phenols and amines may be pentafluorobenzylated. Incorporation of halogens permits the use of gas chromatography with electron capture detection.

Examples of particular analytes that may be derivatized by one or more of the above derivatizing agents are naturally-produced branched and straight chain, lipophilic and hydrophilic carboxylic acids having ten to twenty carbon atoms, phenobarbitol, (a bifunctional compound), 5-ethyl, 5-toluyl barbituric acid, estradiol, N-acyl-serotonin, melatonin, prostaglandin $F_{2a}$, (a hydrophilic carboxylic acid), 2,4-dichloro phenoxy acetic acid, 2,4-dichlorophenol, acetylsalicylic acid, delta-9-tetrahydro-cannabinol, 11-hydroxy-delta-9-tetrahydrocannabinol, etc.

Thus, the above examples clearly demonstrate that short and long chain lipophilic carboxylic acids, long chain hydrophilic carboxylic acids, carboxylic acids of intermediate polarity, organic acids (e.g. the barbiturates), weak organic acids such as phenols, and amines may all be derivatized by the method of the invention. Further, it is clear that polyfunctional compounds (e.g. 11-nor-9-carboxy-$\Delta^9$-tetrahydrocannabinol, which has both carboxylic and phenolic functionalities or cannabidiol which has two phenolic functions) may be derivatized at both groups in good yield (65 to 75% in the case of 11-nor-9-carboxy-$\Delta^9$-tetrahydrocannabinol and 100% in the case of cannabidiol).

The analysis of carboxylic acids and amines is particularly important because it can, for example, result in the rapid identification of microorganisms causing infectious diseases since such compounds are often produced by infectious microorganisms as a result of their normal metabolic processes. Gas chromatographic separation of various low to medium molecular weight metabolites present in infected body fluids, e.g. plasma, cerebrospinal fluid or spent medium, is a known means of identification of the infection. Identification of such bacteria is based upon the gas chromatographic profile of short chain and volatile carboxylic acids produced by the bacteria in high concentrations. This profile is a kind of "fingerprint" because each bacterium has a different profile. Recently, a number of investigators have proposed that monitoring of the longer chain carboxylic acids directly from the fluids of infected patients may be used to confirm infection and identify the bacteria. However, because such longer chain acids are present in very low concentrations, highly sensitive analytical techniques are required and derivatization becomes a necessary preliminary step. An example of a bacterium that can be identified in this way is *Staph. aureus* which can be identified by its profile of lipophilic, branched and straight chain $C_{10}$ to $C_{20}$ fatty acid derivatives present in hydrolysates of the bacterium. The acids identified included the odd numbered fatty acids which are of considerable diagnostic importance because odd numbered fatty acids are not synthesized by mammalian systems and if present in plasma or cerebrospinal fluid are strong indicators of infection.

Similarly analyses for drug, herbicide, pesticide, etc. residues in tissues and body fluids can be carried out. For example, analysis of blood plasma can reveal traces of delta-9-tetrahydro-cannabinol and its metabolite 11-hydroxy-delta-9-tetrahydro-cannabinol.

In the case of prostaglandins, double derivatization (esterification and oximation) is required for adequate analysis by gas chromatography with electron capture detection. It has been found that sequential derivatization is possible by the methods of the invention while the analyte is adsorbed on a single solid resin. Consequently, this enables automation of an analytical technique that was previously quite complex. Thus, the ability to carry out sequential derivatizations is a significant additional advantage of the present invention.

An ideal system for routine clinical analysis would involve the following: fully automated extraction and derivatization; automated gas chromatographic analysis; automated profile analysis and identification of the infectious agents based on these profiles. Automation of gas chromatography is well established, and extensive information exists for computer based profile recognition. The present invention can provide the necessary automated extraction and derivatization.

The extraction/derivatization technique of the invention generally takes place at ambient temperatures (i.e. 15° C. to 30° C., and normally 20° C.), although temperatures up to about 100° C. can be employed if desired as macroreticular resins are generally stable up to at least this temperature. Higher temperatures may, however, reduce the ability of the resin to adsorb the materials, and usually an optimum temperature can be found giving a high rate of reaction with a low rate of desorption. Such optimum temperatures are thus within the range of 0° C. to 100° C., more usually 15° C. to 70° C., and most commonly 15° C. to 60° C., or even 15° C. to 50° C. Operation of the process at ambient temperature is particularly preferred because it eliminates the need for any heating or cooling.

Before impregnating the resin with derivatizing reagent, care should preferably be taken to remove from the resin all manufacturing by-products, such as monomers and inorganic salts which act as preservatives. The resin, which is not itself hydrophilic, should then be wetted with a hydrophilic solvent, e.g. methanol, ethanol or acetonitrile, in order to permit permeation of water into the pores. However, in the case of AMBERLITE ®XAD 2, the amount of the solvent used is preferably less than 40 μl per 100 mg of resin, desirably less than 30 μl per 100 mg, and most preferably about 25 μl per 100 mg. A greater amount of solvent may produce clumping of the resin and variability of the yield.

The macroreticular resins, after suitable preparation, can most conveniently be impregnated by the derivatizing agent prior to use merely by shaking the resin beads with an aqueous solution of the derivatizing agent. If desired, the beads can then be separated from the solution by filtration, dried and packaged in suitable amounts (e.g. 100 mg) ready for use.

This procedure may be modified by forming a saturated solution of the derivatizing agent in contact with further undissolved derivatizing agent. The resin may then be introduced into this solution and agitated, but should be kept out of direct contact with the solid derivatizing agent to make sure that adsorption takes place only from solution. A screen or filter made of glass frit, for example, can be used for this purpose. This allows a greater amount of the reagent to be adsorbed by the resin per unit surface area.

In an alternative procedure, impregnation may take place from a water miscible solvent such as acetonitrile. After allowing the solvent to permeate the pores of the resin, the derivatizing agent may be added, preferably together with NaOH solution.

Impregnation of the reagent in the resin may also be effected by dissolving the reagent in a volatile solvent, e.g. fluorinated hydrocarbons such as FREON ®, saturating the resin with the solution and then evaporating off the solvent in a stream of air. However, deposition from an aqueous solution is the preferred method.

The impregnated resin so prepared can simply be added to an aqueous solution of the analyte and the mixture shaken for a period of time (usually from a few minutes to about an hour). When the reaction has taken place, the resin can easily be separated from the aqueous solution by filtration and is then washed. The unreacted material may be eluted with one solvent and the analyte finally eluted by a second solvent.

Alternatively, a column of the impregnated resin (which may be sold as a pre-packaged unit) can be used as the adsorptive phase for the isolation of the analyte from the aqueous medium. The extraction and derivatization of the analyte takes place as the solution percolates through the column. The column is then sequentially washed with water and appropriate solvents to separately elute the organic reagents and the derivatized analyte. This procedure is particularly well adapted to automation.

If required, the impregnated resin can be made part of a kit intended greatly to facilitate the extraction/ derivatization procedure. For example, the kit may include a measured quantity of the impregnated resin, dosage units of buffer or caustic solution, quantities of eluants for the analyte and reagent, and for the derivatized product, and instructions for use.

It was mentioned above that the use of co-solvents is generally unnecessary. However, a co-solvent may be advantageous when a lipophilic analyte is to be adsorbed and derivatized directly from a biological matrix, e.g. blood plasma. This has become evident from studies carried out on plasma containing delta-9-tetrahydro-cannabinol and its metabolites, e.g. 11-hydroxy-delta-9-tetrahydro-cannabinol. These compounds are lipophilic and occur in plasma in association with lipoproteins. It was found that the presence of the lipoproteins interfere with the efficient extraction of the cannabinoids from the unmodified plasma, but the presence of a co-solvent in the aqueous matrix significantly improved the extraction efficiency. The most effective co-solvent was found to be $CH_3CN$ and it is believed that this shifts the equilibrium so that less of the analyte is protein bound. This shows that adsorption and derivatization directly from biological matrices may encounter problems in particular cases, but that these problems can be overcome when the reasons for the problems are known.

The following examples illustrate the present invention but are not intended to limit its scope in any way.

EXAMPLE 1

Preparation of Macroreticular Resin

Commercially available AMBERLITE®XAD 2 resin was cleaned using procedures recommended by the manufacturer to prepare an active adsorbent surface. The fines were removed by suspension of the commercial product in distilled water, aspiration of the supernatant and repetition of this procedure until the aqueous supernatant was clear. Residual monomeric compounds were removed as follows. The water-washed resin was isolated by filtration and washed sequentially with ethanol and ether. The ether-washed resin was transferred to a Sohxlet apparatus and extracted for several hours with ether. The Sohxlet extracted resin was transferred to a round bottom flask and the solvent was evaporated in vacu at 50° C. The entire procedure removed both organic contaminants as well as inorganic salts present in the commercial product to prevent microbiological growth on the surface of the beads. Standard procedure for storage of resin that has been prepared for use as an adsorbent requires suspension in organic solvent such as acetone or methanol to inhibit microbial growth. This also serves to wet the resin in order to permit subsequent hydration by water. However, for reasons described below, this method of storage and hydration was not appropriate for purposes of preparing a resin which could effect a reaction. Consequently, in order to prevent microbial contamination during storage the cleaned 15 resin was stored dry at −20° C. until used. With these storage conditions reproducible yields were obtained over a period of three weeks with the same batch.

EXAMPLE 2

Impregnation

The following derivatizing agents were used to impregnate the resin by the technique explained below: benzyl bromide (BzBr), pentafluorobenzyl bromide (PFB Br) and methyl iodide.

The dried resin obtained in Example 1 was treated with a volume of ethanol prior to impregnation with derivatizing agent. This was affected by the addition of EtOH followed by vortexing until the beads were again free flowing. Initially, studies were conducted using volume/ weight (v/w) ratios of 0, 10, 25 and 40 μl of EtOH to 100 mg dried resin prior to the addition of derivatizing agent. The standard conditions so developed to give optimum yield used a v/w ratio of 25 μl EtOH to 100 mg resin.

Derivatizing agent was similarly added (i.e. the liquid was added dropwise) and vortexed until it was free flowing. In the case of $CH_3I$, due to the high volatility of the reagent (BP=43° C.), the tube was chilled in an ice bath. The v/w ratio of reagent to resin was determined empirically for each alkylating agent and analyte. Furthermore, the amount of resin used for maximum yield of derivatization was also empirically determined (cf below).

EXAMPLE 3

Derivatization Reaction

Derivatization reactions as explained below were carried out on the following analytes: straight chain carboxylic acids having ten to twenty carbon atoms, phenobarbitol (PB), 5-ethyl, 5-toluyl barbituric acid (ETB) and estradiol (E2). These analytes were obtained from commercial sources.

General reaction conditions were as follows. A quantity of resin appropriate for the reagent and analyte (see Table I below) was weighed and transferred into a 16×100 mm siliconized screw capped glass tube and impregnated in situ by the procedure described in Example 2. Four ml of various aqueous phases were added to the impregnated beads (the compositions of the aqueous phase used with the various analytes are summarized in Table 1).

TABLE 1

Composition of Aqueous Phase for a Given Analyte

| Analyte | Amount | Aqueous Phase |
|---|---|---|
| $C_{10}-C_{20}CO_2H$ | 10 μG | $PO_4^1 = $ : pH 7.4; 0.05M |
| Phenobarbitol (PB) | 25 μG | $CO^2 = $ ; pH 11; 0.05M |
| Estradiol (E2) | 25 μG | 0.1N NaOH |
| Prostaglandin F $_{2\alpha}(PGF_{2\alpha})$ | 50 μG | $PO_4 = $ pH 7.4; 0.05M |

[1]Phosphate Buffer.
[2]Carbonate Buffer.

A 25 μl aliquot containing the analyte in solution was added to each mixture. The amounts of analyte used in the standard procedures (in 25 μl aliquot) are shown in Table 1. The screw capped tubes were sealed with Teflon ®-lined screw caps and the mixtures were shaken at room temperature for one hour at a speed of 175 cycles per minutes (cpm).

The beads were isolated by filtration, and after the phosphate buffer (or NaOH solution for $E_2$) had been drained, the resin was washed with approximately 40 m of water and the excess water was removed by positive air pressure. In the analysis of the straight chain carboxylic acids, E2 and PB, the derivatized analytes were eluted with 10 ml ether. The ether phase was dried with sodium sulfate and the external standards were added to the dry solution. For the straight chain carboxylic acids the external standards were esters of one carbon homologues. For benzylation of E2 the external standard was the benzyl tetracosanoate. For benzylation and methylation of PB the external standard was the dibenzyl and dimethyl derivatives of 5-ethyl-51-toluyl barbituric acid (ETB) respectively. For the pentafluorobenzylation of PB the external standard was the dibenzyl derivative of ETB. It was not possible to separate the dipentafluorobenzyl (di PFB) derivatives of ETB and PB.

In the derivatization of $PGF_{2\alpha}$ the elution of the derivatized product was different. In this case the resin was first washed with 10 ml hexane which removed the benzyl bromide (BzBr) or the pentafluorobenzylbromide (PFBBr) and the esterified $PGF_{2\alpha}$ was subsequently eluted with diethyl ether. The internal standard benzyl tetracosanoate was added to the ether solution.

In all cases the dried ether solutions were transferred to siliconized glass tubes and evaporated to dryness under a stream of nitrogen with warming in a sandbath. The derivatives of the carboxylic acids and PB were taken up in 25 μl of acetonitrile. The derivatives of $PFG_{2\alpha}$ and E2 were taken up in 25 μl BSTFA/TMCS.

The results are shown in Table 2 below:

TABLE 2

| Analyte | Derivatizing Agent | Derivative Formed | Yield (%) |
|---|---|---|---|
| $C_{16}$, $C_{18}$ Acids | PFBBR | PFB Ester | 100 |
| $C_9$–$C_{18}$ Acids | BzBr | Bz Ester | 70–80 |
| PGF2α | BzBr | Bz Ester | 54 |
| | PFBBr | PFB Ester | 100 |
| PB | BzBr | Bz Ether | 85 |
| | PFBBr | PFB Ether | 100 |
| | $CH_3I$ | $CH_3$ Ether | 55 |
| $E_2$ | BzBr | Bz Ether | 70 |

EXAMPLE 4

Table 3 below shows the results of extraction/derivatization directly from plasma which was used as a typical biological matrix, and from buffer solution. One ml plasma containing analyte was buffered with 4 ml buffer to adjust the pH to a value at least 2 log units higher than the pKa of the analyte. The derivatization reaction was then carried out as in Example 3.

TABLE 3

Yield of Benzyl Derivatives from Buffer and Plasma

| Analyte | Yield from Buffer | Yield from Plasma | Yields Ratio of Plasma/Buffer |
|---|---|---|---|
| PGF2α | 54 ± 3 (n = 3)[1] | 55 ± 5 (n = 2) | 100 |
| $E_2$ | 70 ± 2 (n = 2) | 33 ± 2 (n = 2) | 47 |
| 2,3,4 | 84 ± 3 (n = 4)[4] | 14 ± 0.5 (n = 6)[4] | 17 |

[1] Range of n determinations (%).
[2] Samples of PB in plasma (25 μg/ml) prepared in - hour.
[3] Ortho-Bi-Level Kit for quality control yield was determined at 15 and 44 μg/ml.
[4] Structure of Dibenzyl derivative confirmed by GC/MS library match and by the presence of the molecular ion at 412 with a relative abundance of 15%.

As can be seen from Table 3, there is a decrease in yield for some analytes when they are extracted/derivatized from plasma as compared to buffer, but the yield of $PGF_2$ from plasma is the same as from buffer indicating that there is no inhibition by plasma constituents for derivatization of this analyte. This suggests that there is no general "poisoning" of the resin catalyst by the compounds that are present in the biological matrix. The decrease in yield for the other analytes may be due to an effect of plasma constituents on the analytes themselves.

Table 3A below shows the results of similar extraction/derivatization reactions carried out on other analytes. The reaction conditions were the same as those indicated above for the reactions of Table 3.

TABLE 3A

| Analyte | Derivatizing Reagent | Matrix | Yield |
|---|---|---|---|
| NAS[1] | benzyl bromide | Buffer[5] | 30% |
| | | Plasma[6] | 20% |
| 2,4 DPA[2] | benzyl bromide | Buffer | 25% |
| 2,4 DPP[3] | benzyl bromide | Buffer | 7% |

TABLE 3A-continued

| Analyte | Derivatizing Reagent | Matrix | Yield |
|---|---|---|---|
| ASA[4] | benzyl bromide | Buffer | 2% |

[1] N Acetyl Seratonin (NAS)—A neuro transmitter involved in the regulation of sleep.
[2] 2,4 Dichloro Phenoxy Acetic Acid (2,4DPA)—one of a large class of phenoxy acetic acid herbicides used extensively in agriculture and in maintenance of domestic lawns.
[3] 2,4-Dichloro Phenol (2,4-DPP)—a biological transformation product of 2,4 DPA. This phenol is believed to be responsible for many of the environmentally damaging effects of the phenoxyacetic acid herbicides.
[4] Acetylsalicylic Acid (ASA or Aspirin)—a commonly used over the counter anti-pyretic and anti-inflammatory agent.
[5] An aqueous solution of phosphate salts.
[6] Treated in the same way as the plasma used for the reactions of Table 3.

Results show that the simultaneous extraction/derivatization appears to be a general reaction which permits the formation of derivatives of a wide range of organic compounds. The derivatization is not limited to monofunctional analytes, since difunctional analytes, e.g. PB, can be converted to the di-alkyl or dibenzyl derivatives.

EXAMPLE 5

Yield as a Function of the v/w Ratio of Derivatizing Agent to Resin

Two experiments were conducted to determine the optimum v/w ratio of reagent to resin. The first experiment utilized constant volume of derivatizing agent with varying weights of resin. Thus for instance, 50 μl of PFBBr were used to impregnate 75, 100, 200 and 400 mg of resin (dry weight) that had been impregnated with a ¼ v/w ratio of EtOH. In the second experiment the weight of resin was kept constant but varying volumes of derivatizing agent were used. Thus, batches 100 mg of AMBERLITE ®XAD 2 resin (dry weight) were prewetted with 25 μl of EtOH. These were then impregnated with 10, 25, 50 and 75 μl of PFBBr. Both experiments were carried out using PB and C16 and C18 carboxylic acids and $PGF_2$ as analytes. The methylation of PB was investigated using 100 mg resin (dry weight) prewetted with 25 μl EtOH. Batches of this preparation were impregnated with 25, 50, 75 μl of $CH_3I$.

The pentafluorobenzylation and the benzylation of PB was determined at various v/w ratios of reagent to resin. In both cases, optimum yield was obtained at a ratio of 0.25. Pentafluorobenzylation of $PGF_{2\alpha}$ required a v/w ratio of 0.25 for optimum yield. For the derivatization of C16 and C18 carboxylic acids PFBBr required a v/w ratio of 0.5. These optimum values were obtained using both a constant volume of reagent and varying the weight of resin as well as using a constant weight of resin and varying the volume of the reagent, as explained above.

EXAMPLE 6

Yield as a Function of the Weight of Resin Used

Varying amounts of resin were impregnated with a volume of derivatizing agent necessary to give the optimum v/w ratio. For instance, in the case of the benzylation of PB, 100 mg of resin were prewetted with 25 μl of EtOH and impregnated with 25 μl of BzBr; 200 mg of resin were prewetted with 50 μl of EtOH and 50 μl of BzBr etc. The different weights of appropriately impregnated resin were then used in the derivatization reaction. In this experiment the following reactions were studied: methylation of 15 PB; benzylation of PB; benzylation of E₂.

The results are summarized in Table 4 and show an increase in yield with an increase in the amount of resin used.

TABLE 4

| | Yield as Function of Weight of Resin | | |
|---|---|---|---|
| Analyte | Derivatizing Agent | Weight of Resin | Yield (%) |
| PB | CH₃I | 200 | 10 |
| | | 350 | 55 |
| PB | BzBr | 25 | 47 |
| | | 100 | 70 |
| | | 200 | 85 |
| E₂ | BzBr | 25 | 32 |
| | | 50 | 44 |
| | | 100 | 52 |
| | | 200 | 71 |

1. Wetted with EtOH and impregnated at optimum v/w ratios.

EXAMPLE 7

Yield as a Function of Concentration

The benzylation of several analytes was studied over a concentration range to determine if the yield varies linearly with concentration. The range for the C16 and C18 carboxylic acids was from 0.5 to 2.5 $\mu$g/ml in the aqueous phase. The range for PGF$_{2\alpha}$ was 0.25 to 25 $\mu$g/ml in the aqueous phase. The range for PB was 2.5 to 12.5 $\mu$g/ml in the aqueous phase. The range for E2 was 2.5 to 25 $\mu$g/ml in the aqueous phase. In all cases studied the yield was constant with changes in concentration.

EXAMPLE 8

Impregnation Methods

When buffer was added to resin impregnated without prewetting, a substantial fraction of the resin suspended in the buffer. In contrast, when impregnation with alkylating agent was preceeded by EtOH treatment, all of the resin remained at the bottom of the tube. Prewetting with a volume of EtOH had an important effect on the yield of the reaction. The results are summarized in Table 5.

TABLE 5

| | Yield as a Function of Prewetting with EtOH | |
|---|---|---|
| $\mu$l EtOH/100 mg | Yield of Benzyl Ester (%) | |
| XAD2 Resin | C16 Carboxylic Acid | PGF$_{2\alpha}$ |
| 0 | 70 ± 1 (n = 2) | 19 ± 2 (n = 4) |
| 10 | 80 ± 2 (n = 2) | 54 ± 6 (n = 4) |
| 25 | 96 ± 4 (n = 2) | 59 ± 3 (n = 4) |
| 40 | 86 ± 1 (n = 2) | 58 ± 10 (n = 4) |

When the resin was prewetted with less than 40 $\mu$l EtOH/100 mg resin prior to impregnation with derivatizing agent the resin was free-flowing even after the addition of that agent. In these cases there were no visible droplets of derivatizing agent and analysis of the organic solvent eluate (i.e. the 10 ml washes of ether or hexane) of the XAD2 resin indicated that greater than 90% of the derivatizing agent had been adsorbed. However, if the v/w ratio of EtOH to resin was equal to or greater than 40 $\mu$l/100 mg the resin clumped upon the addition of the reagent. The clumps could not be dispersed upon the addition of buffer and shaking. Similar results were obtained if the resin had been stored under organic solvent. In any event, clumping of resin gave variable results for the derivatization of the polar analyte.

EXAMPLE 9

The applicability of the invention to the generation of a gas chromatographic profile of the fatty acids produced by a specific bacterium was tested, as follows.

The macroreticular resin XAD2 available from commercial sources was prepared as described in Example 1. One hundred mg portions of the resin were suspended in 4 ml of FREON ®. Fifty $\mu$l of pentrfluorobenzyl bromide were added to this mixture and the FREON ® was evaporated by shaking in a waterbath at 30° C. for 1 hour. As the volatile FREON ® evaporated, the pentafluorobenzyl bromide was deposited homogeneously on the surface of the resin beads.

The bacterium under test was *Staph. aureus* propagated in vitro. Known amounts of bacteria were transferred to 1 ml portions of 0.1 M aqueous phosphate solution and hydrolyzed by heating in the phosphate solution for one hour at 100° C.

Each hydrolysate solution was diluted to 4 ml with 0.1 M phosphate buffer at pH 7.4. Each diluted solution was transferred to a tube containing the impregnated resin and was shaken for one hour. The resin was isolated by filtration and the pentafluorobenzyl derivatives were eluted with ether. The ether solution was evaporated to dryness, and the residue was reconstituted in toluene and analysed as described below.

Gas chromatographic analysis was carried out using a Hewlett-Packard 5790 gas chromatograph equipped with a gold injector for injection into capillary columns and a frequency pulsed electron capture detector. The output of the electron capture detector was recorded on a Hewlett-Packard 3390 recording integrator.

For comparison, profiles of the same bacterium were produced by derivatizing the hydrolysate solutions with pentafluorobenzyl bromide by a conventional technique (extractive alkylation employing tetrapentylammonium hydroxide as a catalyst).

FIG. 1 shows the gas chromatographic profiles thus obtained. Profiles B-1 and B-2 were obtained by the method of invention from hydrolysate solutions originally containing 2.2×10⁹ organisms (B-1) and 2.2×10⁸ organisms (B-2). Profiles A-1 and A-2 were obtained from hydrolysate solutions originally containing the same respective number of organisms by the extractive alkylation route.

As will be seen from the Figure, the profiles obtained by the method of the invention were substantially identical to those obtained by extractive alkylation, as were the sensitivities. However, the method according to the invention is more suited to automation than extractive alkylation because the former involves solid/liquid phase separation techniques.

EXAMPLE 10

The quantitative determination of delta-9-tetrahydrocannabinol cannabinol ($\Delta^9$-THC) and its metabolites represents an important area of investigation but conventional techniques have the drawback that they are not easy to automate since they require liquid/liquid separations that frequently result in emulsion formation. A test was accordingly carried out to see if the present invention could be applied to the derivatization step.

XAD2 resin was prepared as described in Example 1, and three different impregnation methods were carried out as follows:

(i) Impregnation from volatile organic solvent

Two ml of FREON® were added to 100 mg of XAD2 resin and 100 µl of a 9:1 mixture of trichloroethylene and pentafluorobenzyl bromide was added to the mixture. The mixture was shaken at 30° C. for 30 minutes, thus evaporating the FREON® and depositing the trichloroethylene and pentafluorobenzyl bromide on the resin.

(ii) Impregnation from water-miscible solvent

One ml of acetonitrile was added to 100 mg of XAD2 resin and allowed to stand for 10 minutes to allow the organic solvent to permeate the pores. One hundred µl of the above 9:1 mixture of trichloroethylene and pentafluorobenzyl bromide was added. This water immiscible liquid mixture was impregnated into the pores by the addition of 3 ml of 0.1 N NaOH while vigorously stirring.

(iii) Impregnation from aqueous medium.

Four ml of 30% acetonitrile in 0.1 N NaOH were added to 200 mg of the resin One hundred µl of the 9:1 mixture was added with vigorous stirring.

Derivatization reactions in aqueous solution were then carried out employing the resins impregnated as above by the following method.

Four ml of 0.1 N NaOH in 30% acetonitrile/water was added to the derivatized resin. A known amount of a cannabinoid ($\Delta^9$-THC or its primary in vivo metabolite 11-hydroxy-$\Delta^9$-THC) from the range of 2 µg to 40 was added and shaken for 1 hour. The resin was isolated by filtration, washed with water and the pentafluorobenzyl derivatives of the cannabinoids were eluted with sequential washings of 10 ml of methylene chloride and 20 ml of $Et_2O$. The methylene chloride wash was taken to dryness, thus removing excess pentafluorobenzyl bromide. The subsequent ether washes were added to the same tube and evaporated to dryness. This procedure was necessary because ether contained impurities that reacted directly with pentafluorobenzyl bromide. The residue was treated with 10 µl of silylating solution (trimethylchlorosilane/N,O-bis(trimethylsilyl)trifluoroacetamide in the ratio 9/1) and then diluted with 500 µl toluene. The silylating solution was necessary to reduce the retention time of the pentafluorobenzyl derivative during gas chromatography.

The results showed that efficient extraction and derivatization from aqueous solution was possible using the resins impregnated by all three of the different impregnation techniques.

Figure 2A:
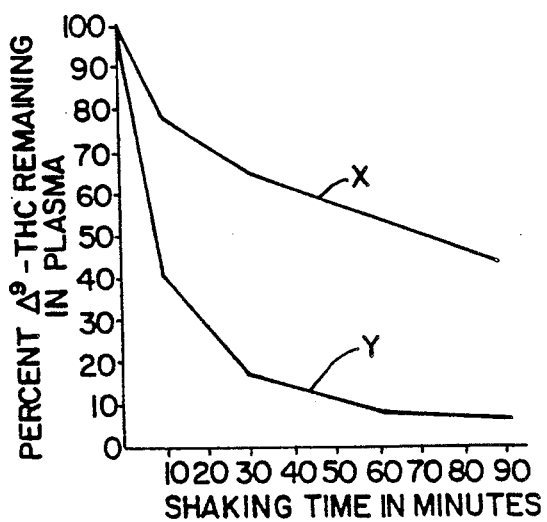
FIGS. 2A and 2B are graphs showing the amount of delta-9-tetrahydro-cannabinol and 11-hydroxy-delta-9-tetrahydro-cannabinol, respectively, absorbed from plasma (curve X) and modified plasma (curve Y) at particular times.
Figure 2B:
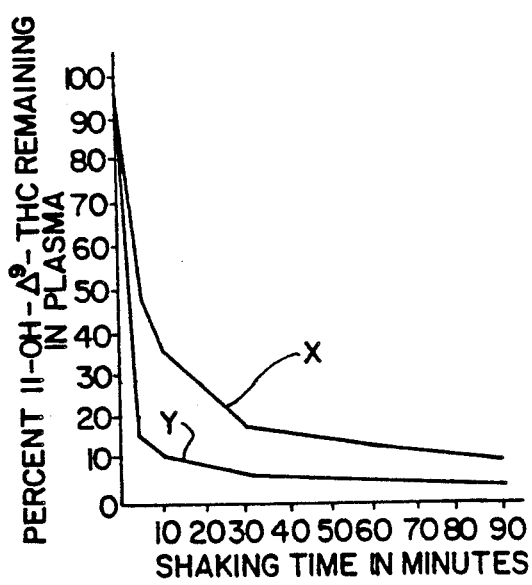

Extraction and derivatization directly from plasma was then attempted, but it was found that the process was inefficient when carried out on unmodified plasma. It was believed that plasma lipoproteins interfered with the extraction of the cannabinoids from the plasma. A number of alternative extraction conditions were investigated, e.g. the effect of saturating the plasma with sodium chloride, acidifying the plasma, and adding acetonitrile as a co-solvent. Only the use of the co-solvent in the aqueous phase had a significant effect on the extraction efficiency as shown in FIGS. 2A and 2B in which curve X represents the extraction from unmodified plasma and curve Y represents the extraction from plasma modified by the addition of 10% acetonitrile. It is believed that the co-solvent makes less of the cannabinoid protein-bond.

The experimental details were as follows. Two hundred mg of impregnated resin were added to 1 ml of plasma containing the cannabinoids and 170 µl of acetonitrile was added. The mixture was shaken for one hour at 75 cycles/minute at room temperature. The plasma was then removed by aspiration and the resin was washed with 4 ml of water. Four ml of 30% $CH_3CN$ in 0.1 N NaOH was added to the washed resin followed by 100 µl of a 9:1 mixture of TCE/PFBBr. The reaction mixture was then shaken for 1 hour at room temperature. The derivatives were then isolated and analysed. The pentafluorobenzyl derivatives were obtained in high yield (85% for $\Delta^9$-THC and 80% for 11-OH-$\Delta^9$-THC).

A polyfunctional cannabinoid (cannabidiol) was also studied. The bis-pentafluorobenzyl derivative was obtained in quantitative yield, demonstrating that the increase in lipophilicity resulting from the addition of one pentafluorobenzyl moiety does not inhibit subsequent pentafluorobenzylation of other reactive functionalities.

EXAMPLE 11

Tests were carried out on the extraction and derivatization of N-acetyl serotonin and melatonin with pentafluorobenzyl bromide prior to analysis by gas chromatography/mass spectrometry with negative ion chemical ionization or gas chromatography/electron capture detection.

The derivatizing agent was impregnated into XAD2 resin by the techniques of the previous examples, and the extraction/derivatization was carried out on relatively pure solutions of the analytes and also on plasma containing the analytes. The relatively pure solutions were prepared by dissolving a known amount of the analyte in 0.1N NaOH. Samples of plasma containing the analytes were first treated with sulphuric acid/sodium tungstate to precipitate the proteins (which were removed by centrifugation) and the supernatant was made alkaline with 0.1N NaOH.

Extraction and derivatization was carried out by shaking the analyte solutions with the resin for one hour at 37° C., separating the resin beads, washing the beads with hexane (which eluted excess derivatizing agent and highly lipophilic pentafluorobenzyl derivatives of, for example, palmitic and stearic acids), and elution of the derivatized analyte with ether. In the case of N-acetyl serotonin as the analyte, the ether was evaporated and the residue reconstituted in trifluoroacetic anhydride and kept at room temperature for 10 minutes. Then the trifluoroacetic anhydride was evaporated and the residue reconstituted in toluene containing an internal standard. The samples were then subjected to analysis.

The trifluoroacetic anhydride was employed in the case of N-acetyl serotonin because it was found that the gas chromatographic properties of the pentafluorobenzyl bromide derivatives were poor, the compounds having prolonged retention times and trailing peaks. Trifluoroacetylation blocks the amide nitrogen and thus decreases the polarity of the molecule resulting in sharp peaks and decreased retention times. However, this results in multiple products since N-acetyl serotonin is a polyfunctional molecule. However, the fact that more than one product is obtained is not an inherent disqualifying factor since the ratio is reproducible.

The results showed that one or two products were formed depending on the reaction conditions, the major one being the O-pentafluorobenzyl derivative. This derivative was produced in good yield and is suitable for highly sensitive determination or analysis.

In the case of melatonin, one derivative was formed, which was to be expected since the compound is monofunctional. The derivative was found to be the pentafluorobenzyl derivative at the indole nucleus. This compound was produced in good yield and is suitable for highly sensitive analysis or determination.

Figure 3:
FIG. 3 is a graph showing the relationship between the quantity of derivatizing agent per unit volume of resin and the yield of derivatized product.

Tests were conducted to see how variations in the amount of pentafluorobenzyl bromide impregnated into the resin affected the yield of the melatonin derivative. It was found that the ratio of volume of pentafluorobenzyl bromide to the weight of resin was a determining factor of yield as can be seen from FIG. 3 of the drawings. Nevertheless, FIG. 3 also shows that the resin plays a catalytic role in forming the derivatives. This is evident from an increase in yield as the ratio of volume of pentafluorobenzyl bromide to amount of resin is decreased.

It was also found that the percentage yield was substantially unaffected by the concentration of the analyte in the starting solution.

The results show that it is feasible to use the method of the invention for the extraction and derivatization of N-acetyl serotonin and melatonin from plasma.

EXAMPLE 12

One hundred milligrams of commercially available AMBERLITE ®XAD 7 resin were prepared for impregnation by the method outlined for XAD 2 resin in Example 1.

The resin was then prewetted with 25 µl of EtOH and 50 µl of benzyl bromide. Four ml of 0.05 M phosphate buffer were added to the impregnated resin. Prostaglandin $F_{2\alpha}$ (50 µg in 100 µl of phosphate buffer) was added to the aqueous phase and the reaction mixture was shaken for one hour. The resin was isolated by filtration and washed with hexane to elute unreacted benzyl bromide. Unreacted prostaglandin $F_{2\alpha}$ was eluted with diethyl ether. Fifty µg of benzyl tetracosanoate (i.e. the benzyl ester of a straight chain carboxylic acid containing 24 carbon atoms) was added to the ether to serve as an external standard. The ether was evaporated to dryness and taken up in trimethyl silylating solutions to form the trimethyl silyl derivative of the benzyl ester of prostaglandin $F_{2\alpha}$. Gas chromatographic analysis of the mixture showed that the yield of benzylated prostaglandin $F_{2\alpha}$ was 40%.

EXAMPLE 13

In this Example, the chromophoric reagent α,p-dibromoacetophenone (DAP) was used to convert $\Delta^9$-tetrahydrocannabinol to a highly chromophoric derivative.

The reaction conditions were identical to those described in Example 10, the amount of DAP used being equimolar to the amount of pentafluorobenzyl bromide used in Example 10.

The reaction product had thin layer chromatography properties and gas chromatographic retention times identical to an authentic standard of the $\Delta^9$-tetrahydrocannabinol-parabromoacetophenone ether synthesized on a semipreparative scale (5 mg) and structurally identified by mass spectrometry.

DAP is conventiontally used for derivatizations used in high pressure liquid chromatographic analysis of organic acids. Thus the present invention lends itself to use with such forms of analysis.

EXAMPLE 14

Gas chromatography/electron capture detection traces were generated for the pentafluorobenzyl ethers of delta-9-tetrahydro cannabinol and 11-hydroxy-delta-9-tetrahydro cannabinol produced by the method of the invention and by a conventional technique i.e. extractive alkylation.

The derivatization according to the invention was carried out using XAD2 resin by the method set forth in Example 10 using an aqueous buffer solution of the cannabinoids as the starting material.

The extractive alkylation was carried out as indicated in the Analytical Chemistry article mentioned in the introduction of this specification using aqueous buffer solutions of the cannabinoids as the starting material. The product of the extractive alkylation reaction was purified by gas chromatography before the GC/ECD trace was produced. This is in contrast to the derivatized product produced by the method of the invention which was used directly to produce the GC/ECD trace.

Figure 4A:
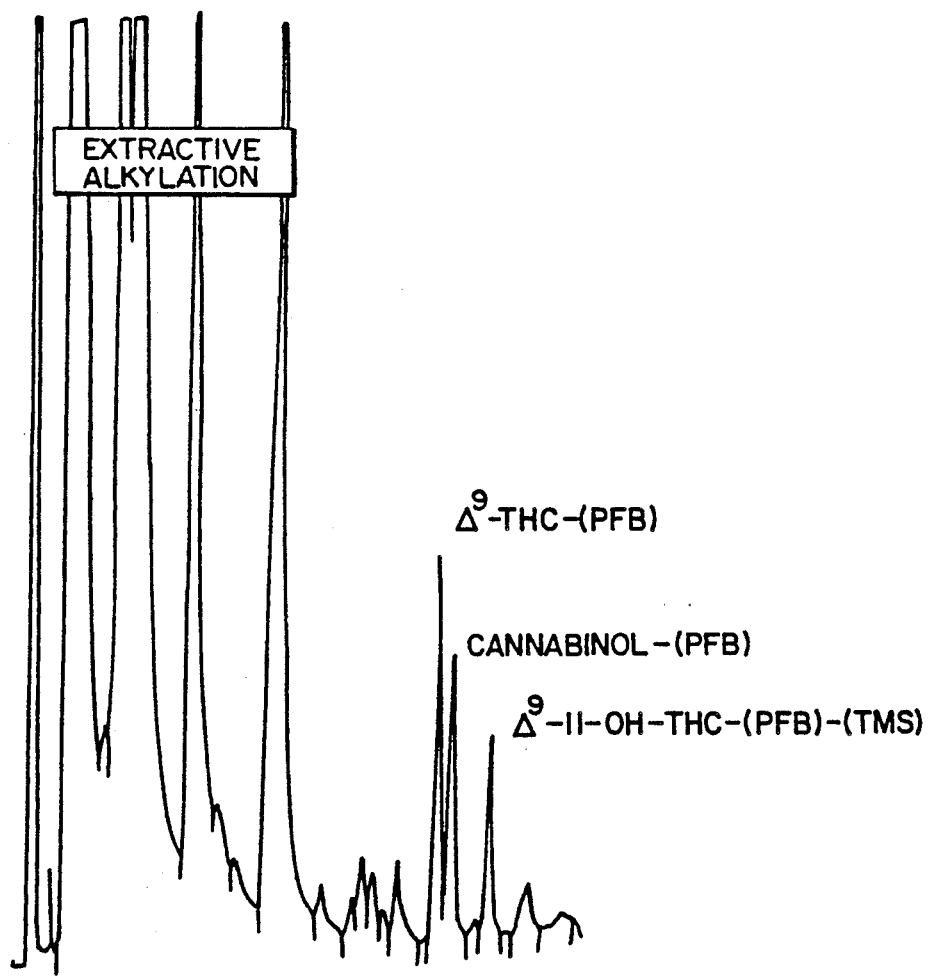
FIGS. 4A and 4B are traces produced by gas chromatography/electron capture detection of derivatives produced by a conventional technique (FIG. 4A) and by the method of the invention (FIG. 4B)
Figure 4B:
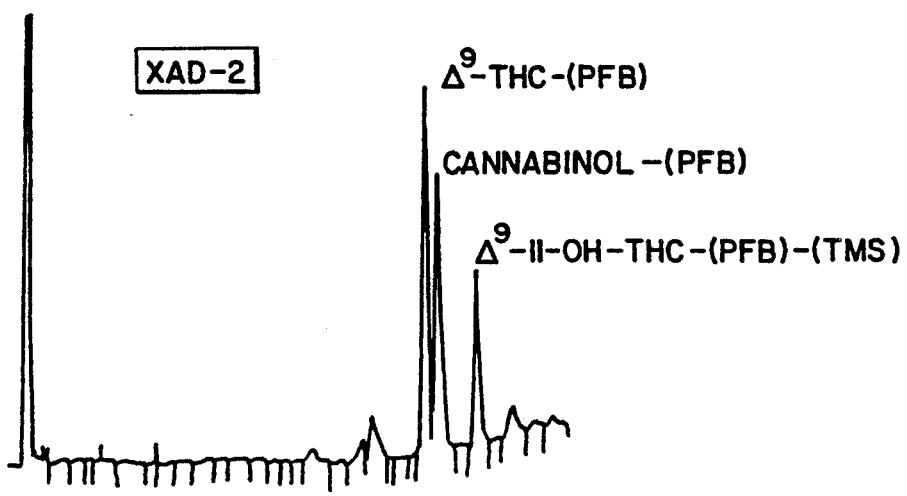

The traces are shown in FIG. 4, FIG. 4a being the trace for the derivatives produced by the conventional techniques and FIG. 4b being the trace for the derivatives produced by the method of the invention.

The striking feature is that the conventional technique, despite attempted purification by column chromatography as a preliminary step, gave a product containing a large amount of impurities (the initial peaks) which were absent in the unpurified product produced by the method of the invention. This is significant because the cleaner product permits the apparatus to be used for a much longer period of time without downtime for cleaning.

The gas chromatography/electron capture detection traces were produced from 1 microgram of cannabinoid at 150°–300° C. at 8°/minute. The chromatographic medium was Chromosorb ®W, 80–100 mesh.

EXAMPLE 15

In order to demonstrate that non-ionic macroreticular resins are effective in the present invention whereas ionic macroreticular resins are not, parallel tests were carried out employing two resins: XAD-2 (a non-ionic resin) and Amberlyst ®15 (a cation exchange resin).

Both resins were treated identically with respect to clean-up and use in reaction. The reagents and reaction conditions were those disclosed in J. CHROMATOGR. 358, 137–146, 1986 by Rosenfeld et al.

All reactions were carried out in replicates of four and reaction product (pentafluorobenzyl pentadecanoate) was found only in those samples where XAD-2 was used as the catalyst. The results are discussed in detail below with reference to FIGS. 5, 6 and 7 of the accompanying drawings, which are gas chromatograms carried out on the product solution.

Figure 5:
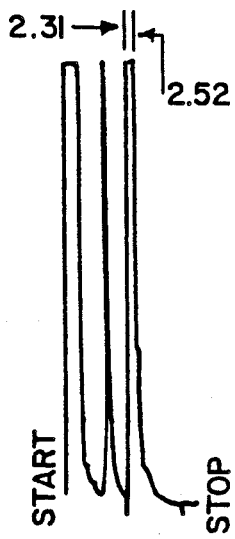
FIGS. 5–10 are also traces produced by gas chromatography/electron capture detection of standard solutions, blanks and samples as explained in Examples 15 to 17 below.

FIG. 5 shows a trace of synthetic standards to identify the retention time of the analyte. The peak at 2.31–2.52 represents pentafluorobenzyl pentadecanoate. The earlier peak is pentafluorobenzyl tridecanoate present in our laboratory calibration solutions as an external standard but not pertinent to this Example.

Figure 6A:
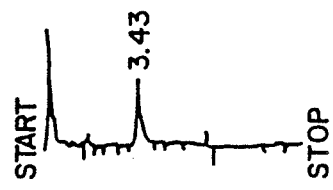
Figure 6B:
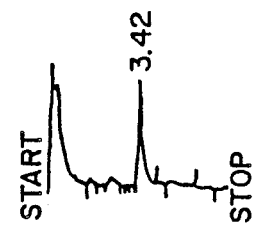

FIG. 6 shows the results of gas chromatography carried out on the product solution resulting from the test employing Amberlyste ®15 resin. Trace A was for a blank preparation (i.e. a reaction carried out with resin and alkylating agent but no analyte) and trace B was for the proper test. In both instances the injection volume was 2 µl out of 500 µl of solution. Although there is a very small peak in trace B that could correspond to the desired product, this peak also occurs in the blank (trace A).

Figure 7A:
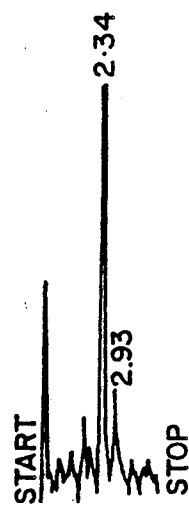
Figure 7B:
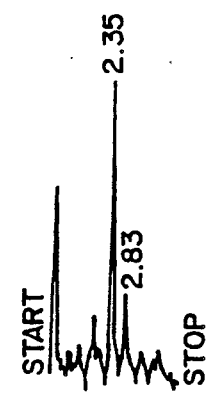

FIG. 7 shows the results of gas chromatography carried out on the product solution resulting from the test employing XAD-2 resin. Trace A was for an injection of 0.5 μl from 500 μl of extract. Trace B was for an injection of 0.5 μl from 1000 μ. Both traces show a strong peak representing the desired product.

It is felt that these results clearly demonstrate that there is no reaction at all when Amberlyste ®15 resin is used and a considerable reaction when XAD-2 serves as the catlyst. Hence, Amberlyste ®15 is not a catalyst resin that is capable of simultaneous isolation and derivatization of organic acids from aqueous media.

EXAMPLE 16

In this Example, prostaglandin $E_2$ ($PGE_2$) was isolated from biological matrix (plasma) and converted to electrophoric derivatives on macroreiicular styrene/divinylbenzene resin. Oximation and pentafluorobenzylation were sequentially carried out on the same resin support.

This dual stage reaction was necessary because the determination of prostaglandins (PG's) by gas chromatography (GC) with electron capture (ECD) or mass spectrometric (MS) detection requires derivatization of multiple functionalities and if the derivatizations are to be automated, it is important to show that most, if not all, of the required derivatizations can be carried out on a solid support, and preferably on a single solid support. The experimental details are as follows.

Apparatus

Derivatized analytes were determined on a Hewlett Packard 5790 gas chromatograph equipped with a pulse linearized electron capture. The output of the detector was monitored and recorded on a HP 3390A integrator. Gas chromatography was carried out on a J & W DB-1 column with a length of 30 m, an inner diameter of 0.23 mm and a film thickness of 0.15 um. The carrier gas was hydrogen with a linear velocity of 40 cm/min at 200° C. Make up gas was 10% argon in methane at a flow rate of 15 mL/minute. Low resolution mass spectra were determined on a VG micromass magnetic sector instrument under similar gas chromatographic conditions. A supelco vacuum module was purchased from Supelco (Canada) Oakville, Ontario.

Reagents

Pentafluorobenzyl bromide (PFBBr) and Pentafluorobenzyl hydroxylamine hydrochloride (PFBHOX) were purchased from Caledon Laboratories, Georgetown, Ontario. For derivatization, a solution of PFBHOX in pyridine was prepared at a concentration of 10 mG/mL. The macroreticular resin XAD-2, a crosslinked copolymer of styrene/divinylbenzene was purchased from BDH Laboratories, Toronto, Ontario and prepared for use as a support by methods described previously in J. CHROMATOGR. 358, 1986, 37, Rosenfeld et. al. Solvents were obtained from the usual commercial suppliers such as Fisher and BDH Canada. Natural $PGE_2$ and $C^{-14}$ labeled $PGE_2$ ($C^{-14}$ $PGE_2$) at a specific activity of 56.9 mCi/mmole were purchased from Sigma and Amersham International (U.K.) respectively. The second carbonyl containing PG 6-keto PGF was also purchased from Sigma. The Supelclean LC-18 cartridges and Florosil were obtained from Supelco (Canada), Oakville, Ontario.

Derivatization of pure analyte

All reactions were carried out in 16×100 mm screw cap vials which were capped with Teflon lined caps during reaction. In Adsorption Procedure A the analyte was added to 200 mG resin dissolved in 1 mL of acetonitrile and adsorbed by addition of 8 mL water acidified with acetic acid and shaking the solid/aqueous mixture for 15 minutes at room temperature. The aqueous phase was aspirated and 5 mL of hexanes was added to the resin. The mixture was vortexed and the liquid phase was again aspirated. The resin was then set in a stream of dry nitrogen and maintained at 60° C. for approximately 20 min. until the resin beads were freely mobile which is a physical characteristic of the dry resin. Two hundred μL of PFBHOX solution was added and the resin was heated to 60° C. for three hours or overnight at 40° C. The resin was washed with water acidified to pH 3.5 with acetic acid; the aqueous phase again being removed by aspiration. Four mL of phosphate buffer at pH 7.4 were added followed by 100 μL of solution of PFBBr in 1,1,2 trichloroethylene (TCE) (1/9 v/v) and the reaction mixture was shaken for two hours at 40° C. in a water bath. The resin was isolated by filtering the mixture through a plug of silanized glass wool in a 5 mL pipetteman tip, washed thoroughly with water then with hexanes. The isolation of derivatized analyte was carried by two separate procedures. In both procedures the resin was isolated by filtering the mixture through a plug of glass wool in a 5 mL pipetteman tip and washing thoroughly with water and with hexanes. In the first variation of the basic procedure, the analytes were eluted with 10% ethanol in ether and evaporation of the eluting solvent. The second procedure involved an in-line purification on Florosil. Accordingly, the resin was first washed with hexanes to remove the PFBBr and subsequently the pipetteman tip containing the resin was transferred to the top of a second pipetteman tip containing 1 cm of Florosil. The "linked" columns were washed with $CH_2Cl_2$ which was discarded and then washed with 10% $EtOH/Et_2O$ which eluted derivatized analyte.

An additional modification of the above procedure was also investigated. In Adsorption Procedure B, $PGE_2$ was added to a tube containing 200 mG resin and 4.0 mL distilled water. The aqueous phase was acidified with 90 μL acetic acid and the analyte was adsorbed by shaking at room temperature for 15 min. then the resin was isolated by aspiration using a 20 gauge needle. Derivatization at the carbonyl and carboxylic acids was carried out as described above and purification was effected on a column of Florosil.

For isolation of $PGE_2$ from plasma as derivatized product the analyte was first separated from the aqueous and proteinaceous matrix using a Supelclean LC-18 cartridge. A 1 mL LC-18 cartridge, set in a Supelco Vacuum Module, was prewetted with 2 mL of $CH_3CN$ and then washed with 5 mL of distilled water. One mL of plasma was diluted with 4 mL of water and acidified with 90 μL of acetic acid. This mixture was transferred to the head of the cartridge and drawn through the extracting LC-18 phase with vacuum. The cartridge was washed with acidified water and then with hexanes; both washings being discarded. A 16×100 mm test tube containing 200 mG resin was placed in the Vacuum Module to receive the analyte which was eluted from the LC-18 cartridge with 1 mL of $CH_3CN$. Subsequently $PGE_2$ was adsorbed onto the resin using Procedure B, oximinated with PFBHOX and esterified with PFBBr on XAD-2; finally the mixed derivative was purified on Florosil. These procedures are described in detail above.

Gas Chromatoqraphic Analysis

Prior to injection the external standard, PFB tetradecanoate, was added to the injection solution in 10 μL of anhydrous toluene. For 250 nG $PGE_2$ the isolate was dissolved in 50 μL of BSTFA/TMCS (9/1 v/v) and 0.5 μG of PFB tetradecanoate added. One to two μL of this solution were injected using an on-column injection technique. The initial temperature of the oven was 215° C. and this was programmed to 290° C. at a rate of 4° C./min. There was no time delay at the lower temperature and a 3 minute delay at 290° C. The retention time of the minor isomer was 16.73 minutes, for the major isomer it was 17.53 min. and for the external standard the retention time was 12.94 min.

Thin layer chromatography

Thin layer chromatography was carried out on silica gel plates and developed in a solvent system of with the following v/v composition: 55 Toluene/45 Ethyl Acetate/2.5 Methanol/2.0 Acetic Acid. Radiolabel was identified by autoradiography and authentic derivative was identified by Iodine staining.

Calculation of Yield

Yield was calculated from recovery of $C-14$ $PGE_2$, followed by thin layer chromatography of the products, determining the fraction of recovered radiolabel that co-chromatographed with authentic mixed derivative. The overall recovery of product by was obtained by multiplying this fraction by the total radiolabel recovered. Where the objective was to compare recoveries of the derivatives from different matrices the yield was calculated relative to extractive alkylation from buffer with PFBBr as the reagent and subsequent derivatization with PFBHOX in solution. This procedure had been previously shown to give 80 to 100% yield for pure prostaglandin in aqueous solution. While not as accurate as the radiolabel method for determining recoveries this approach was taken for reasons of cost radiolabeled material and the inherent instability of the analyte in both native and radiolabeled forms.

Derivatization from buffer was also attempted with XAD-21 a product made by Rohm and Haas. This material has the same chemical composition as XAD-2 but has been prepared synthetically with a mesh size of 100-120. Because of the fine mesh size, aspiration was difficult and water could not be efficiently removed by this technique. Consequently the oximination procedure had to be modified. Specifically the removal of water under the stream of nitrogen was replaced by warming at 40° C. for 18 hours.

Results and Discussion

The reaction was first investigated with derivatization of pure analyte from simple matrices. Secondly, any possible effect of matrix components on the yield of the reactions was investigated. Thus $PGE_2$ was isolated and derivatized from buffer by direct adsorption/derivatization. In the case of biochemical incubate (buffer containing 10% fetal calf serum and lung fibroblasts) and plasma, however, both direct adsorption/derivatization and by pre-isolation of analyte by reverse phase chromatography were utilized. In most cases samples were purified on Florosil as this technique was expected to be a standard feature of most analytical methods. The results are summarized in Table 6.

The effect of the matrix on the entire process is mainly seen in the precision of the recovery from plasma. If the analyte is adsorbed directly from plasma the recovery (determined relative to extractive alkylation with PFBBr and oximination in solution) is 30% but the relative standard deviation is 20%. Precision of recovery (relative to extractive alkylation with PFBBr and oximination in solution) from plasma is markedly improved by pre-isolation of $PGE_2$ on a reverse phase column (Table 6). The considerable amount of product lost in the Florosil clean-up can be recovered by elution with $CH_3CN$. This isolate, however, is heavily contaminated with an insoluble material which makes gas chromatographic analysis difficult by blocking syringes and thus elution with $CH_3CN$ to increase recovery was not used in the procedure.

TABLE 6

Isolation and derivatization of $PGE_2$ as the mixed Pentafluorbenzyloxime/Pentafluorobenzyl ester product from different matrices.

| Adsorption Matrix (volume of matrix) | Amount $PGE_2$ in nG (117,000 cpm of $C-14$) | % Yield[1] Without Florosil Clean-up | % Yield[1] With Florosil Clean-up |
|---|---|---|---|
| Acidified water/$CH_3CN$ (8 mL) | 250/$C-14$ | 56 +/− 7 | 42 +/− 13[2] |
| Buffer (4 mL) | 62.5/$C-14$ | | 40 +/− 6.5[2] |
| Plasma (1 mL) | 250/$C-14$ | | 27 +/− 12[2] |
|  | $C-14$ | | 30 +/− 12[2] |
|  | 250 | | 35 +/− 7[3] |
|  | 50 | | 31 +/− 12[3] |
| Biochemical Incubate (1 mL) | 250 | | 34 +/− 8[3] |
|  | 50 | | 34 +/− 8[3] |

[1]Average +/− relative standard deviation (n = 6).
[2]Yield calculated from recoveries of radiolabel.
[3]Yield calculated relative to extractive alkylation with PFBBr and oximination in solution.

Determination of yield by recovery of radiolabel or comparison to regular derivatization procedures gave similar results. The yield of the mixed derivative was moderate but this is not uncommon for the prostaglandins particularly when the starting matrix is a biological sample and chromatographic purification is a part of the sample preparation. The reduced yield is not due to unreacted $PGE_2$. Without a Florosil clean up 80% of the radiolabel is recovered; less than 2% of this material is unreacted starting material. Another 3% is reaction product that is less polar than the mixed derivative and is probably the derivative of the common degradation products of $PGE_2$ i.e. PGA, B or C series of prostaglandins. Approximately 15% of recovered radiolabel is an unidentified product. Despite the moderate yield a linear calibration curve was obtained from 20 to 300 nG/mL using biochemical incubate as a matrix.

The process was tested by the determination of $PGE_2$ from incubate of human lung fibroblasts using tissue from normal volunteers and from patients with fibrotic lung disease. Concentrations from such 12 samples were found in the range 20 to 300 nG/mL. This was the range expected for the analyte in such biological samples.

Derivatization on XAD-21 required prolonged heating of the native $PGE_2$ with the ketone functionality unprotected and cumbersome aspiration methods. Despite this the desired product was recovered although in a highly variable yield of approximately 20–30% from buffer. The variability of the yield is not surprising given the fact that the appropriate apparatus had not yet been designed. This work however demonstrates the feasability of using other resins of this class.

In summary the use of a solid supported sample preparation scheme incorporating isolation from matrix, reaction at two positions of PGE$_2$ and in-line purification is feasible. While there is a matrix effect this can be circumvented by an appropriate clean-up technique but it is one frequently used in the analysis of prostaglandins.

Figure 8A:
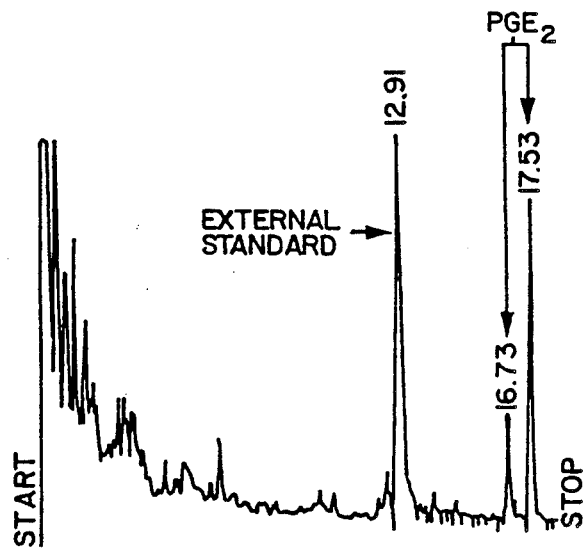
Figure 8B:
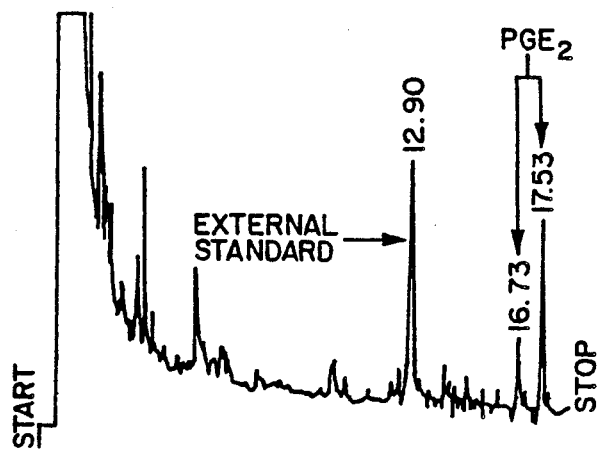

FIG. 8 shows gas chromatogram traces of the derivatives prepared on the XAD-2 resin and isolated with a Florosil clean-up (trace A) and without a Florosil clean-up (trace B).

EXAMPLE 17

The determination of the urinary metabolite of delta-9-tetrahydrocannabinol (THC) (the active component of marijuana and hashish) involves complex problems because both acid and phenolic functionalities are present on the same molecule and previous experience has shown that carboxylic acids from biological matrices are selectively suppressed by solvents employed. Thus the carboxylic acid moieties on the analyte may cause a reduction of the reactivity of the entire molecule. In the present Example, tests were carried out to see if this would be the case or whether the different functionalities on the molecule would react independently.

Experimental

Four mL of urine spiked with COOH-THC to a concentration of 750 nG/mL was added to 200 mG resin. The aqueous phase was acidified and the compound was adsorbed and derivatized as previously described in Anal Chem. 58 716 and 3044, 1986 by Rosenfeld et. al. for absorption and derivatization of THC from plasma. Derivatization was carried out using both 1,1,2-Trichloroethylene (TCE) and pentanol as solvents for the reagent. At the completion of the reaction the 200 mG of resin was washed and cleaned as described by Rosenfeld et al. The 5 mL pipetteman tip containing the cleaned sample of resin was placed in 5 mL pipetteman tip containing 2 cm of Florosil. This "linked" column was washed with 12 mL CH$_2$Cl$_2$ and 12 mL 10% ethanol in ether (EtOH/Et$_2$O) with the eluates being kept separate. The solvents were evaporated and the residue taken up in 50 μL silylating solution. Prior to injection this solution was diluted to 500 μL with toluene and 1 μG of the calibration standard pentafluorbenzyl (PFB) tetracosanoate was added. A 1-2 μL aliquot was injected for gas chromatographic analysis.

Results

Figure 9A:
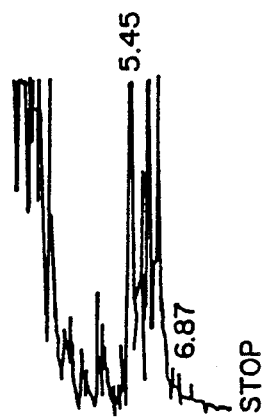
Figure 9B:
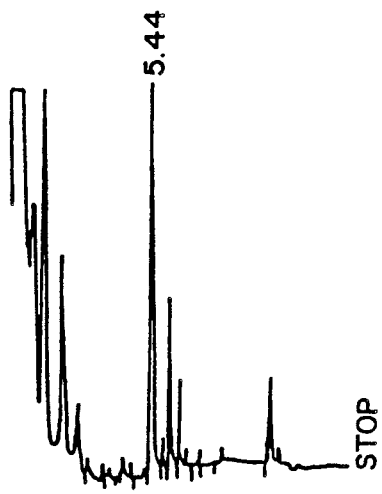
Figure 9C:
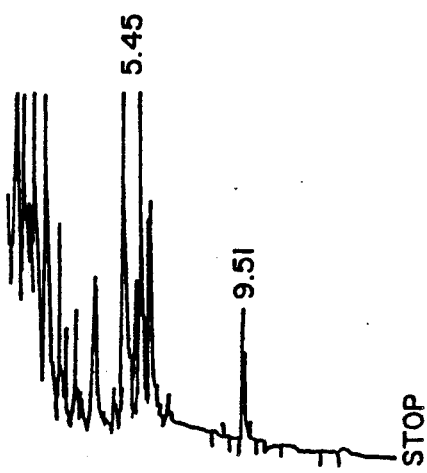
Figure 10A:
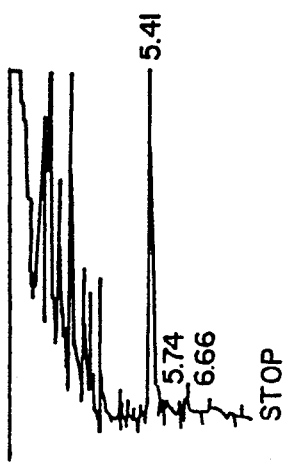
Figure 10B:
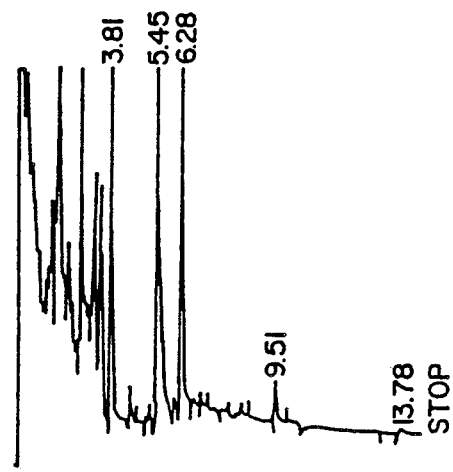
Figure 10C:
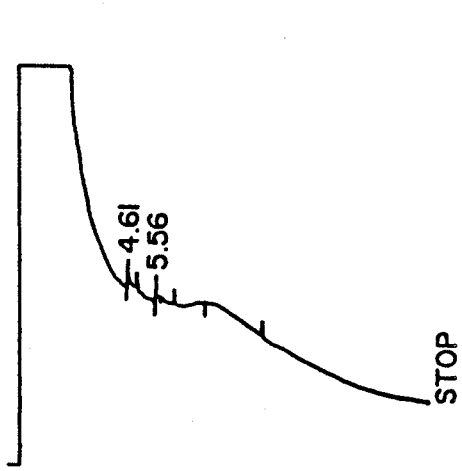
Figure 10D:
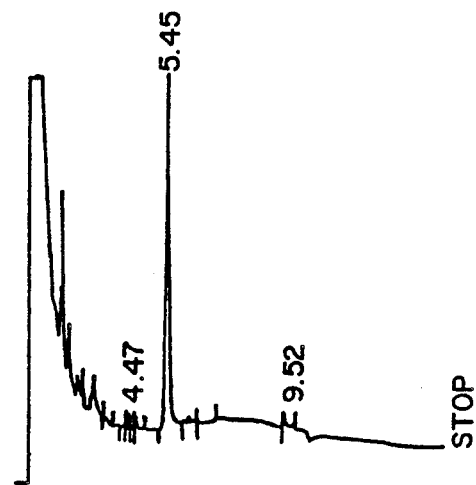

FIG. 9 shows the traces of the analyses using TCE as a solvent for the reagent PFBBr. Trace (A) represents the EtOH/Et$_2$O fraction of a blank sample consisting of 4 mL of unspiked urine; trace (B) represents the CH$_2$Cl$_2$ fraction of the sample; and trace (C) represents the EtOH/Et$_2$O fraction of the sample. The peak that appears at 9.51 minutes in both the CH$_2$Cl$_2$ and EtOH/Et$_2$O eluates is the product of a bis pentafluorbenzylation with reaction occuring at both phenolic and carboxylic acid functionalities. Although not as clear because of interferences there is a peak in the EtOH/Et$_2$O elute at 6.28 that corresponds to the reaction product formed by reaction of the phenolic moiety. A blank trace is provided for comparison and demonstrates that there is some endogenous compound which can result in a false positive to the mono-PFB derivative.

Calculation of yields of the various products was not carried out because of the unavailability of radiolabeled material. Nevertheless it is already apparent that in the presence of urine constituents, considerable mono PFb derivative is formed. This is in contrast to the case of plasma where apparently high yield of a single product is obtained under similar circumstances. The data is, perhaps, not surprising. Urine contains many oxidation products of exogenous and endogenous organic molecules and, it should be noted in relatively high concentrations. We have demonstrated that one such class, the alcohols, are inhibitors of the reaction of the carboxylic acid functionality.

FIG. 10 shows similar traces for the case where pentanol was used as a diluent. Trace (A) represents the EtOH/Et$_2$O fraction of a blank sample consisting of 4 mL of unspiked urine; trace (B) represents the EtOH/Et$_2$O fraction of the sample; trace (C) represents the CH$_2$Cl$_2$ fraction of a blank sample consisting of 4 mL of unspiked urine; and trace (D) represents the CH$_2$Cl$_2$ fraction of a sample. There is very low yield of the bis PFb product but considerable mono PFB product resulting from the specific reaction at the phenolic position. Moreover use of pentanol suppresses the formation of interferences that chromatograph in the region of the mono PFB product. Thus, in the presence of pentanol, the reaction mixture is shifted predominantly to one product, thus simplifying the analyses and providing a cleaner isolate than that obtained in the case where TCE is a solvent. In particular, the use of pentanol seems to suppress the formation of the interference at 6.28. This data also shows that unlike the bis PFB derivative which fractionates between both eluate fractions the mono PFB product is eluted only in the EtOH/Et$_2$O fraction. This is probably due to the free carboxyl group which increases the polarity and thus retention on a normal phase chromatographic system. This increased polarity and acid functionality can be exploited in optimizing the separation technology to further purify the extract prior to instrumental analysis.

I claim:

1. A process for converting an organic compound, having a reactive group, dissolved at a concentration of 50 μg/ml or less in an aqueous solution into a derivative thereof which is suitable for analysis or determination by techniques requiring the presence in the derivative of a detectable radical selected from the group consisting of a chromophore, a fluorophore and an electrophore, which process comprises contacting said organic compound in said aqueous solution at a temperature in the range of 15°–40° C. in substantially non-acidic conditions with a derivatizing agent capable of reacting with said reactive group in the presence of a catalyst to introduce said detectable radical into the organic compound, said catalyst being a water-insoluble, non-ionic macroreticular resin capable of absorbing the organic compound and the derivative from aqueous solution, and said resin being selected from the group consisting of styrene-divinylbenzene copolymers and cross-linked methacrylate copolymers.

2. A process according to claim 1 wherein said resin is a styrene-divinylbenzene copolymer.

3. A process according to claim 1 wherein said organic compound is selected from the group consisting of carboxylic acids, phenols and amines.

4. A process according to claim 1 wherein said organic compound is selected from the group consisting of straight chain carboxylic acids having ten to twenty carbon atoms, phenobarbitol, 5-ethyl-5-toluyl-barbituric acid, estradiol, N-acyl-serotonin, melatonin, prostaglandin F$_{2\alpha}$, 2,4-dichlorophenoxy-acetic acid, 2,4-dichlorophenol and acetylsalicyclic acid.

5. A process according to claim 1 wherein said organic compound is obtained from a biological matrix.

6. A process according to claim 1 wherein said aqueous solution is a biological matrix.

7. A process according to claim 1 wherein said organic compound has a plurality of reactive groups and each group is sequentially derivatized by sequentially contacting said resin having said compound adsorbed thereon with different derivatizing agents, each capable of derivatizing a different one of said reactive groups.

8. A process according to claim 1 wherein said derivatizing agent is selected from the group consisting of benzyl bromide, pentafluorobenzyl bromide, methyl iodide and $\alpha$,p-dibromoacetophenone.

9. A process according to claim 1 wherein said resin is pre-treated to render its surfaces wettable by said aqueous solution by contacting the resin with a hydrophilic organic solvent.

10. A process according to claim 9 wherein the organic solvent is selected from the group consisting of ethanol and acetonitrile each used in an amount of 40 ml or less per 100 g of resin.

11. A process according to claim 1 wherein said resin is employed as a chromatography medium after said derivatization reaction has taken place in order to separate the derivative from the starting material and impurities.

12. A process according to claim 1 wherein the resin is impregnated with the derivatizing agent prior to said derivatizing reaction.

13. A process according to claim 12 wherein the resin is impregnated by a method selected from the group consisting of (i) directly adding the derivatizing agent to the pre-treated resin with shaking, (ii) contacting the pretreated resin with an aqueous solution of the derivatizing reagent, and (iii) contacting the resin with a solution of the derivatizing agent in a volatile solvent followed by evaporation of the solvent.

14. A process according to claim 1 wherein said aqueous solution contains a plurality of said organic compounds to be derivatized.

15. A process according to claim 1 wherein said resin is located in a chromatography column and said aqueous solution is fed through said column in order to effect said derivatizing reaction.

16. A process according to claim 15 wherein said derivatizing reaction is carried out in an automated system which automatically feeds a measured amount of said aqueous solution to the chromatography column and then feeds washing solutions and/or eluants necessary to separate the derivative form starting materials and impurities.

17. A process according to claim 1 wherein said organic compound is derived from a microorganism that is pathogenic to man and/or animals.

18. A process according to claim 17 wherein a plurality of said organic compounds are present and, following said derivatizing reaction, the derivatives are subjected to gas chromatographic profile analysis in order to identify said microorganism.

19. A process for derivatizing a carboxylic acid to prepare said carboxylic acid for analysis or determination, comprising contacting an aqueous solution of said carboxylic acid having a concentration of said acid of 50 μg/ml or less with pentafluorobenzyl bromide at a temperature in the range of 15°–40° C. in substantially non-acidic conditions in the presence of an insoluble, non-ionic, chemically unreactive macroreticular resin, selected from the group consisting of polystyrene-divinylbenzene copolymers and cross-linked polymethacrylate copolymers, the surface of said resin being wetted by the solution, whereby said resin acts as an absorbent for both said carboxylic acid and said pentofluorobenzyl bromide and as a catalyst for the derivatization reaction therebetween.

20. A process according to claim 1 wherein the organic compound to the derivatized is a compound containing a carboxylic acid group and another reactive group and wherein said derivatization is carried out in the presence of an alcohol to inhibit the reactivity of the carboxylic acid group so that derivatization proceeds selectively at said other group.

21. A process according to claim 20 wherein said organic compound is the metabolite of tetrahydro-cannabinol, said other group being a phenolic group of said compound.

22. A process according to claim 21 wherein said alcohol is pentanol.

* * * * *